United States Patent
Kimura et al.

(10) Patent No.: US 9,987,359 B2
(45) Date of Patent: Jun. 5, 2018

(54) SUBCUTANEOUS INJECTION PRODUCT FOR CATTLE FOR INDUCING SUPEROVULATION

(71) Applicant: Kyoritsu Seiyaku Corporation, Tokyo (JP)

(72) Inventors: Koji Kimura, Okayama (JP); Shuichi Matsuyama, Tochigi (JP); Kenyo Ishii, Ibaraki (JP); Makoto Seki, Tokyo (JP); Toshiya Hamada, Saitama (JP)

(73) Assignee: Kyoritsu Seiyaku Corporation, Tokyo (JP)

( * ) Notice: Subject to any disclaimer, the term of this patent is extended or adjusted under 35 U.S.C. 154(b) by 0 days. days.

(21) Appl. No.: 14/907,165

(22) PCT Filed: May 23, 2014

(86) PCT No.: PCT/JP2014/063672
§ 371 (c)(1),
(2) Date: Jan. 22, 2016

(87) PCT Pub. No.: WO2015/011977
PCT Pub. Date: Jan. 29, 2015

(65) Prior Publication Data
US 2016/0250333 A1 Sep. 1, 2016

(30) Foreign Application Priority Data

Jul. 22, 2013 (JP) .................. 2013-151440

(51) Int. Cl.
| | |
|---|---|
| *A61K 38/09* | (2006.01) |
| *A61P 5/02* | (2006.01) |
| *A61P 15/08* | (2006.01) |
| *A61K 47/02* | (2006.01) |
| *A61K 38/24* | (2006.01) |
| *A61K 9/00* | (2006.01) |
| *A61K 35/02* | (2015.01) |

(52) U.S. Cl.
CPC ............ *A61K 47/02* (2013.01); *A61K 9/0019* (2013.01); *A61K 35/02* (2013.01); *A61K 38/24* (2013.01)

(58) Field of Classification Search
None
See application file for complete search history.

(56) References Cited

U.S. PATENT DOCUMENTS

| | | |
|---|---|---|
| 5,162,306 A | 11/1992 | Donaldson |
| 5,589,457 A | 12/1996 | Wiltbank et al. |

FOREIGN PATENT DOCUMENTS

| | | | |
|---|---|---|---|
| EP | 0276166 A2 | | 7/1988 |
| JP | 2004-203750 A | | 7/2004 |
| JP | 2004203750 A | * | 7/2004 |
| JP | 2005-281245 A | | 10/2005 |
| JP | 4408017 B2 | | 2/2010 |

OTHER PUBLICATIONS

Isozaki et al. "Superovluation in Japanese black cown by a single subcutaneous administration of FSH, 1: Changes in concentration of porcine FSH in plasma and superovulatory response following a single subcutaneous administration of porcine FSH with aluminum hydroxide gel suspension" 2007.*

HogenEsch H "Mechanism of immunopotentiation and safety of aluminum adjuvants" Frontiers in Immunology 3:Article 406. Published Jan. 10, 2013.*

Kimura et al. "Successful superovulation of cattle by a single administration of FSH in aluminum hydroxide gel" Theriogenology 68:633-639. Published 2007.*

International Search Report issued in PCT/JP2014/063672 dated Aug. 19, 2014 (2 pages).

Kimura, K. et al.; "Successful superovulation of cattle by a single administration of FSH in aluminum hydroxide gel"; ScienceDirect, Theriogenology, vol. 68, 2007, pp. 633-639 (7 pages).

Kimura, K. et al.; "Method for Inducing Superovulation in Cattle by Using Aluminum Hydroxide Gel by Single Administration"; The Japanese Society Zootechnical Science Annual Meeting abstracts, VII 30-8, vol. 103rd, Mar. 20, 2004, p. 123 (2 pages).

Isozaki, Y. et al.; "Superovulation in Japanese Black Cow by a Single Subcutaneous Administration of FSH. (1) Changes in Concentration of Porcine FSH in Plasma and Superovulatory Response Following a Single Subcutaneous Administration of Porcine FSH with Aluminum Hydroxide Gel Suspension"; Bulletin of Fukuoka Agriculture Research Center 26, 2007, pp. 61-64 (4 pages).

Extended European Search Report issued in corresponding European Application No. 14829440.8, dated Nov. 17, 2016 (6 pages).

* cited by examiner

*Primary Examiner* — Christina Bradley
*Assistant Examiner* — Zachary J Miknis
(74) *Attorney, Agent, or Firm* — Osha Liang LLP

(57) ABSTRACT

The present invention provides a subcutaneous injection product for cattle for inducing superovulation characterized by comprising aluminum hydroxide gel and an efficient amount of a gonadotropin, wherein the concentration of the aluminum hydroxide is, in terms of the amount of aluminum, higher than or equal to 0.2 mg/mL and lower than 1.0 mg/mL, which is a subcutaneous injection product that is useful for producing good calves and that can induce superovulation in a cow by a single administration. The present invention also provides a method for producing good calves undergoing steps of subcutaneously injecting the aforementioned injection product into a cow to thereby induce superovulation, inducing estrus in the cow, conducting artificial insemination, and then collecting fertilized eggs.

13 Claims, No Drawings

SUBCUTANEOUS INJECTION PRODUCT FOR CATTLE FOR INDUCING SUPEROVULATION

TECHNICAL FIELD

The present invention relates to a subcutaneous injection product, which gives cattle a little stress and which can induce superovulation in cattle by a single administration, a kit for preparing such an injection product, and a method for producing good calves comprising a step of subcutaneously injecting such an injection product into cattle.

BACKGROUND ART

In a livestock business of cattle, to produce good calves a method comprising collecting internally fertilized eggs from a cow and transplanting the fertilized eggs into other cows is employed. Therefore, a method is performed, in which method a gonadotropin preparation is administered to a cow to induce superovulation, artificial insemination is conducted, and then fertilized eggs are collected.

Conventionally, at the practice of the above-described method, the gonadotropin preparation was administered to the cow multiple times. However, the multiple administrations of the gonadotropin preparation not only give the cow a lot of stress, but also give a lot of strain to veterinaries.

Therefore, the present inventors proposed, as disclosed in a bulletin of Japanese Patent No. 4408017, a preparation for cattle for inducing superovulation, which can induce superovulation by a single administration, and a method for producing good calves comprising a step of administering to cattle such a preparation for inducing superovulation. This preparation for inducing superovulation comprises aluminum hydroxide gel and a gonadotropin. The concentration of the aluminum hydroxide in this preparation for inducing superovulation is, in terms of the amount of aluminum, 1.0 to 5.0 mg/mL, and the administration dose per cattle is 10 to 50 AU in terms of the gonadotropin and 2 to 20 mL as an amount of the preparation for inducing superovulation. Thus, per cattle and per administration, 2 to 100 mg, in terms of the amount of aluminum, of aluminum hydroxide is administered. In the examples of the bulletin of Japanese Patent No. 4408017, the concentrations of the aluminum hydroxide in the preparations for inducing superovulation are, in terms of the amount of aluminum, 1.28 mg/mL and 1.44 mg/mL, the total amounts of the aluminum hydroxide per administration are, in terms of the amount of aluminum, 6.4 to 14.4 mg. Also, the method for producing good calves, which is disclosed in the examples of the bulletin of Japanese Patent No. 4408017, comprises administering to a cow the preparation for cattle for inducing superovulation by intramuscular injection.

Here, there are subcutaneous, intradermal and intramuscular routes as administration ones of a medicament by injection. A bulletin of Japanese Patent Laid-open No. 2005-281245 discloses subcutaneously administering to an animal once a sustained-release formulation for follicle-stimulation that comprises aluminum hydroxide gel and a follicle stimulation hormone, although it is a method comprising inducing superovulation in an experimental animal such as a rabbit. In the bulletin of Japanese Patent Laid-open No. 2005-281245, the concentration of the aluminum hydroxide in the sustained-release formulation for follicle-stimulation is, in terms of the amount of aluminum, 1 to 10 mg/mL, and the total amount of the aluminum hydroxide per administration is, in terms of the amount of aluminum, 0.1 to 50 mg. Moreover, in the examples, the concentration of the aluminum hydroxide is, in terms of the amount of aluminum, 3 mg/mL, and the total amount of the aluminum hydroxide per administration is, in terms of the amount of aluminum, 4.5 mg.

In a bulletin of Fukuoka Agriculture Research Center 26, an examination result is disclosed, wherein the result was obtained by subcutaneously administering to a cow once a preparation obtained by adsorbing a follicular stimulating hormone derived from porcine to aluminum hydroxide gel, and then evaluating the transition of the concentration of the follicular stimulating hormone derived from porcine in plasma of the cow. In this examination, the concentration of aluminum is 1.3 mg/mL, and the single administration dose per cattle is 30 AU in terms of the follicular stimulating hormone and 12.5 mL or 5 mL as a volume of the subcutaneous injection product. Thus, the total amount of the aluminum hydroxide is, in terms of the amount of aluminum, 16.25 mg or 6.5 mg.

As stated above, aluminum hydroxide has been used to release the gonadotropin slowly. However, an appropriate concentration of the aluminum hydroxide in the gonadotropin preparation and an appropriate total amount of the aluminum hydroxide in the single administration have not necessarily been studied.

SUMMARY OF THE INVENTION

Problem To Be Solved by the Invention

The present inventors have administered the preparation for cattle for inducing superovulation comprising aluminum hydroxide gel, which was proposed in the bulletin of Japanese Patent No. 4408017, to a cow by an intramuscular injection. However, if superovulation can be induced by an administration via subcutaneous injection as disclosed in the bulletin of Japanese Patent Laid-open No. 2005-281245 and the bulletin of Fukuoka Agriculture Research Center 26, stress against cattle can be reduced moreover.

Additionally, in the case of intramuscular injection, induration may occur at the site of injection. We have a policy not to use such site where induration occurred as an edible meat. By employing a subcutaneous injection, a problem of contamination of the site of induration into the edible meat can also be avoided.

It has not been studied the concentration and the total amount of aluminum hydroxide, by which concentration and amount there occurs a side effect a little and an appropriate effect can be obtained when the preparation for cattle for inducing superovulation comprising aluminum hydroxide gel is administered via a subcutaneous injection. Because the gonadotropin is an active ingredient, there is an appropriate administration dose for inducing superovulation. Contrary aluminum hydroxide is an auxiliary agent for having the gonadotropin sustained-release. Therefore, it is thought that it is desired to use the aluminum hydroxide at a little amount possible under the condition that the aimed effects can be produced.

The present invention has been accomplished under these circumstances. It aims to provide a subcutaneous injection product comprising aluminum hydroxide and a gonadotropin, which can induce superovulation in a cow by a single administration, a kit for preparing such an injection product, and a method for producing good calves comprising a step of subcutaneously injecting such an injection product into cattle.

Means for Solving the Problem

The present inventors have extremely studied to provide a subcutaneous injection product which can induce superovulation in a cow by a single administration. As a result, they have accomplished the present invention.

Namely, the present invention relates to a subcutaneous injection product for cattle for inducing superovulation, characterized by comprising aluminum hydroxide gel and an efficient amount of a gonadotropin, wherein the concentration of the aluminum hydroxide is, in terms of the amount of aluminum, higher than or equal to 0.2 mg/mL and lower than 1.0 mg/mL.

Also, the present invention relates to a kit for preparing the above subcutaneous injection product for cattle for inducing superovulation according to the present invention, (1) comprising a first container in which the aluminum hydroxide gel is enclosed, a second container in which the gonadotropin is enclosed, and a third container in which a liquid for dissolving the gonadotropin is enclosed, or (2) comprising a first container in which the aluminum hydroxide gel is enclosed, wherein the concentration of the aluminum hydroxide is, in terms of the amount of aluminum, higher than or equal to 0.2 mg/mL and lower than 1.0 mg/mL, and a second container in which the gonadotropin is enclosed.

Further, the present invention relates to a method for producing good calves characterized by comprising a step of subcutaneously injecting into a cow the above subcutaneous injection product for cattle for inducing superovulation according to the present invention, a step of inducing estrus and conducting artificial insemination, and a step of collecting fertilized eggs. Hereafter, the "fertilized eggs" may be referred to as "embryos."

Effect of the Invention

By the present invention, when artificial insemination is conducted to a cow, stress that is given to the cow will be extremely decreased. Also, workload of veterinaries will be reduced.

In the present invention, the injection site is subcutaneous, and it is possible to reduce the administration amount of aluminum hydroxide or the injection product per se. Therefore, an effect can also be obtained, in which swelling and induration difficultly occur at the injected site. The site where swelling or induration has occurred is disposed when the cow is used as an edible meat. Thus, if there is no swelling or induration, percentage of effective use as the edible meat will be increased.

Embodiments for Performing the Invention

The injection product of the present invention is one for a subcutaneous injection. It comprises aluminum hydroxide gel and a gonadotropin.

The aluminum hydroxide gel that is used in the present invention is a suspension liquid. One example is the aluminum hydroxide gel that was listed in Japanese Pharmacopoeia (the 6th edition). The aluminum hydroxide gel may be one that has been prepared by any preparation method. One example of the preparation method is as follows: First, an aqueous solution of aluminum chloride or potassium aluminum sulfate dodecahydrate having an appropriate concentration is prepared. To this solution, an aqueous sodium hydroxide solution is added to adjust the pH to be about 6 to 7, thus obtaining a gel. Thereafter, water is added to be a desirable aluminum concentration. Alternatively, the gel can also be prepared by adding aqueous ammonia to an aqueous solution of ammonium aluminum sulfate dodecahydrate to form a precipitate of aluminum hydroxide, removing supernatant, washing the residual precipitate with distilled water (washing is performed until there is no residual ammonia by nesslerizing), and adding to the washed precipitate phosphate buffered saline or physiological saline Moreover, the gel can also be prepared by the following method: An aqueous sodium hydroxide solution is added to an aqueous solution of potassium aluminum sulfate dodecahydrate to adjust the pH to be about 6 to 7. The liquid thus obtained is centrifuged and supernatant is removed. Distilled water is added to the residual precipitate and the container is fully shaken. The steps of centrifugation, removing of supernatant, and addition of water are repeated. Sodium chloride is added to the liquid thus obtained to be dissolved. An aqueous sodium hydroxide solution is added to adjust the pH to be about 6 to 7. Moreover, water is added.

The aluminum hydroxide gel thus obtained is subjected to sterilization. The sterilization is preferably performed by a method with autoclave. However, the sterilization may be performed by adding a fungicide or a preservative to the aluminum hydroxide gel.

In the injection product of the present invention, the concentration of the aluminum hydroxide is, in terms of the amount of aluminum, higher than or equal to 0.2 mg/mL and lower than 1.0 mg/mL, preferably 0.2 to 0.8 mg/mL, and more preferably 0.3 to 0.6 mg/mL. If the concentration in terms of the amount of aluminum is lower than 0.2 mg/mL, the adsorption of the gonadotropin may come to be insufficient. If the concentration is higher than or equal to 1.0 mg/mL, swelling may occur at the site of injection.

The total amount of the aluminum hydroxide that is contained in one dosage amount of the injection product according to the present invention is, in terms of the amount of aluminum, more than or equal to 1.0 mg and less than 5.0 mg, preferably 1.0 o 4.5 mg, and more preferably 1.5 to 3.0 mg. If the total amount of the aluminum hydroxide that is contained in one dosage amount is, in terms of the amount of aluminum, is less than 1.0 mg, the adsorption of the gonadotropin may come to be insufficient. If the total amount is more than or equal to 5.0 mg, swelling may occur at the site of injection. If a liquid injection product is prepared in an amount, for example, of twice administrations (for administering to two cows), the total amount of aluminum hydroxide that is contained in the prepared liquid injection product is twice the above amount.

As the gonadotropin, follicle stimulating hormone (its abbreviation is FSH), of which amount is usually represented by AU (Armour unit), is used. However, another gonadotropin may be used, which expresses any biological valence that corresponds to the AU. To induce adequate superovulation, about the dosage amount, the injection product having one administration dose for one cow contains preferably FSH of 10 to 50 AU, and more preferably FSH of 20 to 40 AU. Therefore, if a liquid injection product is prepared in an amount, for example, of twice administrations (for administering to two cows), the total amount of the gonadotropin that is contained in the prepared liquid injection product is twice the above amount. Although the form of the gonadotropin is not specifically restricted, one example is freeze dry powder.

One administration dose of the injection product for one cow is preferably 2 to 20 mL, more preferably 2.5 to 8 mL, and specifically preferably 3 to 5 mL. If it is less than 2 mL, adequate amounts of the gonadotropin and the aluminum hydroxide may not be contained in the injection product. To the contrary, if it exceeds 20 mL, the injection causes cattle pain.

The kits for preparing the subcutaneous injection product of the present invention for preparing the subcutaneous injection product for cattle for inducing superovulation according to the present invention are a kit (1) comprising a first container in which aluminum hydroxide gel is enclosed, a second container in which a gonadotropin is enclosed, and a third container in which a liquid for dissolving the gonadotropin is enclosed, and a kit (2) comprising a first container in which aluminum hydroxide gel is enclosed, wherein the concentration of the aluminum hydroxide is, in terms of the amount of aluminum, higher than or equal to 0.2 mg/mL and lower than 1.0 mg/mL, and a second container in which a gonadotropin is enclosed. These kits can also comprise other constitutional members such as an outer packaging material (for example, an outer casing) into which all members that constitute the above kit are packed and an instruction in which a method for using or the like is described.

Here, the "container" may be one that can internally enclose a material (a solid, a liquid, or the like). Examples of the container include an ampule or a vial made of glass or a plastic, and a polymer pouch. The "liquid for dissolving the gonadotropin" is a liquid that is commonly used for preparing an injection product, such as physiological saline and various buffers, and that can dissolve the gonadotropin.

In the kit (1), the aluminum hydroxide concentration of the aluminum hydroxide gel that is a constitutional member of the first container in which the aluminum hydroxide gel is enclosed is higher than that of the subcutaneous injection product for cattle for inducing superovulation according to the present invention. The aluminum hydroxide concentration in terms of the amount of aluminum may come equal to or higher than 0.2 mg/mL and lower than 1.0 mg/mL by mixing in an appropriate ratio the aluminum hydroxide gel and the liquid for dissolving the gonadotropin (with the proviso that the gonadotropin has been added to the liquid), which are constitutional members of the kit (1). Therefore, when the kit (1) is used, the subcutaneous injection product for cattle for inducing superovulation of the present invention is usually prepared by first dissolving the gonadotropin in the liquid for dissolving it, and then mixing the obtained solution and the aluminum hydroxide gel in an appropriate ratio.

In the kit (2), the aluminum hydroxide concentration of the aluminum hydroxide gel that is a constitutional member of the first container in which the aluminum hydroxide gel is enclosed is the same as that of the subcutaneous injection product for cattle for inducing superovulation of the present invention. Therefore, when the kit (2) is used, the subcutaneous injection product for cattle for inducing superovulation of the present invention is prepared by directly dissolving the gonadotropin in the aluminum hydroxide gel.

Both the kit (1) and the kit (2) are not necessarily those, of which constitutional members are suitable to prepare an injection product having a dose for a single administration (for one cow). For example, it may be a constitution by which an injection product having a dose for twice administrations (for two cows) can be prepared. When the injection product having a dose for twice administrations (for two cows) is prepared, one half of the amount of the injection product thus prepared is administered to one cow.

The method for producing good calves of the present invention comprises a step of subcutaneously injecting into a cow the injection product of the present invention, a step of inducing estrus and conducting artificial insemination, and a step of collecting fertilized eggs. The injection product of the present invention is usually administered only one time. The site where the subcutaneous injection is practiced is not restricted. However, because disposal amount of edible meat does not increase even if swelling occurs, the site is preferably around neck. Generally, the injection product of the present invention is subcutaneously administered to a cow in a luteal phase, at 48 to 72 hours later prostaglandin $F_{2\alpha}$ is administered for the purpose of, for example, induction of ovulation, estrus is induced and then artificial insemination is conducted, and at 6 to 8 days later fertilized eggs (embryos) are collected. The fertilized eggs (embryos) thus collected are transplanted to other cows and are grown.

EXAMPLES

Hereafter, the present invention will be particularly explained with reference to examples.

Example 1

Preparation of Aluminum Hydroxide Gel (No. 1)

Aluminum chloride, 14.85 g in terms of an anhydrous one, was dissolved in water to prepare an aqueous solution of 400 mL. Separately, about 5.0 g of sodium hydroxide was dissolved in water to prepare an aqueous solution having an appropriate concentration. The aqueous sodium hydroxide solution was gradually added to the aqueous aluminum chloride solution, thereby adjusting the pH to be 6.5 to 6.6. Thereafter, water was added so that the total volume became 1 L. The concentration of the aluminum hydroxide is, in terms of the amount of aluminum, 3 mg/mL (theoretical value).

The aluminum hydroxide gel thus prepared, 100 mL, was put into a vial having a 100 mL-volume, and the vial was closely sealed with a rubber stopper and an aluminum cap. It was sterilized at 105 degrees Celsius for 30 minutes in an autoclave. After the sterilization, the content of the vial was homogeneously mixed. It was used as an aluminum hydroxide gel in the following experiments.

Example 2

Preparation of Aluminum Hydroxide Gel (No. 2)

Potassium aluminum sulfate, 28.74 g in terms of an anhydrous one, was dissolved in water to prepare an aqueous solution of 400 mL. Separately, about 5.0 g of sodium hydroxide was dissolved in water to prepare an aqueous solution having an appropriate concentration. The aqueous sodium hydroxide solution was gradually added to the aqueous potassium aluminum sulfate solution, thereby adjusting the pH to be 6.4 to 6.6. This liquid was centrifuged (about 3,000 rpm; 5 minutes), and supernatant was removed. To the residue, water having a same volume as that of the removed supernatant was added and then the container was sufficiently shaken. The steps of centrifugation, removal of supernatant, and addition of water were repeated again. Thereafter, 9.0 g of sodium chloride was added and dissolved. The aqueous sodium hydroxide solution was added, thereby adjusting the pH to be 6.4 to 6.6. Further, water was added so that the total volume became 1 L. The concentration of the aluminum hydroxide is, in terms of aluminum, 3 mg/mL (theoretical value). The aluminum hydroxide gel thus prepared was put into a vial and sterilized in the same manner as that in Example 1.

Experiment 1

Assay to Investigate Effects of Concentration and Total Amount of Aluminum Hydroxide for Superovulation 1. Preparation of Injection Product The aluminum hydroxide gel (concentration in terms of aluminum: 3 mg/mL) prepared in Example 1 was diluted with a physiological saline to be concentrations in terms of aluminum of 0.6 mg/mL, 0.3 mg/mL, and 0.15 mg/mL. In 5 mL of each of the aluminum hydroxide gel solutions thus prepared having respective concentrations, 30 Armour unit (A.U.) of Antrin R-10 (a gonadotropin from anterior pituitary (FSH) manufactured by Kyoritsu Seiyaku Corporation) was dissolved. Thus, four injection products were prepared. Concentrations of aluminum hydroxide (concentrations in terms of aluminum) and total amounts of aluminum hydroxide (total amounts in terms of aluminum) of these injection products were as those shown in Table 1.

2. Administration of Injection Product, Artificial Insemination, and Collection of Fertilized Eggs Six Japanese Black Beef cows constituted one group. First, 5 mL of an injection product having a concentration of 3 mg/mL in terms of aluminum was subcutaneously injected into the neck region of each cow. Forty-eight hours later, prostaglandin $F2_\alpha$ was administered. After the onset of estrus, artificial insemination was conducted. After 7 days of the insemination, embryos were collected. After a lapse of 40 days or more from the collection of the embryos, the same treatment as that described above was practiced, except that another injection product having a concentration of 0.6 mg/mL in terms of aluminum was used. Thereafter, similarly, the same treatment as that described above was practiced, except that another injection product having a concentration of 0.3 mg/mL in terms of aluminum or still other injection product having a concentration of 0.15 mg/mL in terms of aluminum was used, wherein there was similarly an interval of 40 days or more between treatments.

3. Results

Table 1 shows the results. As is clear from Table 1, in the case where the concentration of aluminum hydroxide (concentration in terms of aluminum) of the injection product was 0.15 mg/mL, the number of transplantable embryos was significantly small By contrast, in the cases where the concentrations were 0.30 mg/mL or more and within the range that was examined in this experiment, there were no significant difference in the number of large ovarian follicles in estrus, the number of corpora luteum, the number of residual ovarian follicles, the number of embryos collected, and the number of transplantable embryos, even if the concentration was increased.

TABLE 1

| Aluminum hydroxide in injection product | | Condition of cows | | | | | |
|---|---|---|---|---|---|---|---|
| Conc. in terms of aluminum (mg/mL) | Total amount in terms of aluminum (mg) | Number of cows treated | Number of large ovarian follicles in estrus | Number of corpora luteum | Number of residual ovarian follicles | Number of embryos collected | Number of transplantable embryos |
| 3.00 | 15.00 | 6 | 19.0 ± 3.5 | 10.7 ± 2.9 | 2.8 ± 0.9 | 7.5 ± 2.9 | 4.8 ± 1.6 |
| 0.60 | 3.00 | 6 | 20.0 ± 4.3 | 11.7 ± 1.6 | 3.0 ± 1.2 | 8.0 ± 1.3 | 4.3 ± 1.4 |
| 0.30 | 1.50 | 6 | 24.8 ± 6.6 | 11.7 ± 3.8 | 5.3 ± 1.0 | 9.3 ± 2.9 | 4.8 ± 1.7 |
| 0.15 | 0.75 | 6 | 24.2 ± 6.7 | 10.7 ± 3.7 | 3.8 ± 1.5 | 7.7 ± 1.5 | 1.2 ± 0.5 |

Experiment 2

Assay to Investigate Effect of Concentration of Aluminum Hydroxide for Superovulation The same experiment as that of Experiment 1 was practiced, expect that the concentrations of aluminum hydroxide (concentrations in terms of aluminum) in the injection products and the administered amounts were revised to be the values shown in Table 2, and that the number of Japanese Black Beef cows subjected to the experiment were revised to be the values shown in Table 2. Table 2 shows the results. When the total amounts of aluminum hydroxide (total amounts in terms of aluminum) were same to each other, the case where the concentration of aluminum hydroxide (concentration in terms of aluminum) was the highest (1.5 mg/mL) gave the fewest number of transplantable embryos.

TABLE 2

| Injection product | | | Condition of cows | | | | | |
|---|---|---|---|---|---|---|---|---|
| Conc. of aluminum hydroxide in terms of aluminum (mg/mL) | Administered amount (mL) | Total amount of aluminum hydroxide in terms of aluminum (mg) | Number of cows treated | Number of large ovarian follicles in estrus | Number of corpora luteum | Number of residual ovarian follicles | Number of embryos collected | Number of transplantable embryos |
| 1.5 | 1 | 1.5 | 6 | 22.2 ± 7.3 | 10.5 ± 4.1 | 3.3 ± 1.4 | 6.0 ± 2.7 | 2.8 ± 1.3 |
| 0.5 | 3 | 1.5 | 6 | 19.0 ± 6.3 | 10.7 ± 2.9 | 5.2 ± 2.3 | 7.5 ± 2.9 | 6.2 ± 2.9 |
| 0.3 | 5 | 1.5 | 4 | 16.5 ± 4.7 | 8.5 ± 4.9 | 4.5 ± 0.5 | 7.5 ± 4.4 | 5.8 ± 3.5 |

Experiment 3

Measurement of Sizes of Swellings or Indurations

In Experiment 1, the sizes of swellings and/or indurations at the sites (neck regions) where the injection products of the present invention were administered via subcutaneously injection were measured with time. Table 3 shows the results. It is clear from Table 3 that the swelling or induration comes to be large if the concentration of aluminum hydroxide (concentration in terms of aluminum) in the injection product is high and the total amount of aluminum hydroxide (total amount in terms of aluminum) is large.

TABLE 3

| Aluminum hydroxide | | | Size of swelling or induration (mm) | | | | | |
|---|---|---|---|---|---|---|---|---|
| Conc. in terms of aluminum (mg/mL) | Total amount in terms of aluminum (mg) | Number of cows treated | 5 days later the administration | | 10 days later the administration | | 20 days later the administration | |
| | | | Length | Width | Length | Width | Length | Width |
| 3.00 | 15.00 | 6 | 84.4 ± 9.8 | 32.2 ± 8.0 | 73.2 ± 7.4 | 30.8 ± 6.8 | 64.6 ± 5.4 | 17.6 ± 2.0 |
| 0.60 | 3.00 | 6 | 41.3 ± 2.8 | 16.5 ± 0.3 | 38.8 ± 3.0 | 16.5 ± 2.7 | 25.3 ± 5.4 | 12.8 ± 2.5 |
| 0.30 | 1.50 | 6 | 36.7 ± 7.0 | 21.2 ± 1.7 | 42.4 ± 3.8 | 12.0 ± 2.1 | 29.8 ± 4.0 | 11.5 ± 2.4 |
| 0.15 | 0.75 | 6 | 35.2 ± 7.8 | 18.0 ± 5.3 | 21.8 ± 7.4 | 9.2 ± 3.2 | 12.0 ± 5.4 | 6.2 ± 2.6 |

The invention claimed is:

1. A subcutaneous injection product for cattle for inducing superovulation, characterized by comprising aluminum hydroxide gel and gonadotropin present in an amount effective to induce adequate superovulation, wherein the concentration of the aluminum hydroxide is, in terms of the amount of aluminum, 0.3 to 0.6 mg/mL.

2. The subcutaneous injection product for cattle for inducing superovulation according to claim 1, wherein the total amount of the aluminum hydroxide is, in terms of the amount of aluminum, 1.5 to 3.0 mg per administration.

3. The subcutaneous injection product for cattle for inducing superovulation according to claim 1, wherein the content of the gonadotropin is 10 to 50 Armour Units or an amount of any biological valence that corresponds to 10 to 50 Armour Units per administration.

4. A kit for preparing the subcutaneous injection product for cattle for inducing superovulation according to claim 1, comprising a first container in which the aluminum hydroxide gel is enclosed, a second container in which the gonadotropin is enclosed, and a third container in which a liquid for dissolving the gonadotropin is enclosed.

5. A kit for preparing the subcutaneous injection product for cattle for inducing superovulation according to claim 1, comprising a first container in which the aluminum hydroxide gel is enclosed, wherein the concentration of the aluminum hydroxide is, in terms of the amount of aluminum, 0.3 to 0.6 mg/mL; and a second container in which the gonadotropin is enclosed.

6. A method for obtaining fertilized eggs characterized by comprising a step of subcutaneously injecting into cattle the injection product according to claim 1, a step of inducing estrus and conducting artificial insemination, and a step of collecting fertilized eggs.

7. A kit for preparing the subcutaneous injection product for cattle for inducing superovulation according to claim 2, comprising a first container in which the aluminum hydroxide gel is enclosed, wherein the concentration of the aluminum hydroxide is, in terms of the amount of aluminum, 0.3 to 0.6 mg/mL, and wherein the total amount of the aluminum hydroxide is, in terms of the amount of aluminum, 1.5 to 3.0 mg per administration, and a second container in which the gonadotropin is enclosed.

8. A kit for preparing the subcutaneous injection product for cattle for inducing superovulation according to claim 3, comprising a first container in which the aluminum hydroxide gel is enclosed, wherein the concentration of the aluminum hydroxide is, in terms of the amount of aluminum, 0.3 to 0.6 mg/mL, and a second container in which the gonadotropin is enclosed, wherein the content of the gonadotropin is 10 to 50 Armour Units or an amount of any biological valence that corresponds to 10 to 50 Armour Units per administration.

9. The subcutaneous injection product for cattle for inducing superovulation according to claim 2, wherein the content of the gonadotropin is 10 to 50 Armour Units or an amount of any biological valence that corresponds to 10 to 50 Armour Units per administration.

10. A kit for preparing the subcutaneous injection product for cattle for inducing superovulation according to claim 2, comprising a first container in which the aluminum hydroxide gel is enclosed, a second container in which the gonadotropin is enclosed, and a third container in which a liquid for dissolving the gonadotropin is enclosed.

11. A kit for preparing the subcutaneous injection product for cattle for inducing superovulation according to claim 3, comprising a first container in which the aluminum hydroxide gel is enclosed, a second container in which the gonadotropin is enclosed, and a third container in which a liquid for dissolving the gonadotropin is enclosed.

12. A kit for preparing the subcutaneous injection product for cattle for inducing superovulation according to claim 9, comprising a first container in which the aluminum hydroxide gel is enclosed, a second container in which the gonadotropin is enclosed, and a third container in which a liquid for dissolving the gonadotropin is enclosed.

13. A kit for preparing the subcutaneous injection product for cattle for inducing superovulation according to claim 9, comprising a first container in which the aluminum hydroxide gel is enclosed, wherein the concentration of the aluminum hydroxide is, in terms of the amount of aluminum, 0.3 to 0.6 mg/mL, and wherein the total amount of the aluminum hydroxide is, in terms of the amount of aluminum, 1.5 to 3.0 mg per administration, and a second container in which the gonadotropin is enclosed, wherein the content of the gonadotropin is 10 to 50 Armour Units or an amount of any biological valence that corresponds to 10 to 50 Armour Units per administration.

\* \* \* \* \*